United States Patent

Plavnik et al.

[11] Patent Number: 5,818,599
[45] Date of Patent: Oct. 6, 1998

[54] APPARATUS AND METHOD FOR ACCELERATED TESTING OF MATERIALS

[75] Inventors: Gennady Plavnik, Buffalo Grove; Richard N. Schultz, Chicago, both of Ill.

[73] Assignee: Atlas Electric Devices Co., Chicago, Ill.

[21] Appl. No.: 828,313

[22] Filed: Mar. 28, 1997

[51] Int. Cl.[6] .................................................. G01N 21/00
[52] U.S. Cl. .................... 356/440; 356/220; 356/218; 356/213; 356/437
[58] Field of Search .................................. 356/220, 218, 356/437, 440, 213

[56] References Cited

U.S. PATENT DOCUMENTS 4,049,383  9/1977  Burton ................................. 422/52 X
4,350,495  9/1982  Broutman et al. .

FOREIGN PATENT DOCUMENTS

8-193943  7/1996  Japan .

*Primary Examiner*—Frank G. Font
*Assistant Examiner*—Reginald A. Ratliff
*Attorney, Agent, or Firm*—Gerstman, Ellis & McMillin, Ltd.

[57] ABSTRACT

An apparatus and method for the testing of materials by thermal oxidation is provided. The apparatus comprises a housing having at least one optic-isolated chamber. A photon counting photomultiplier and a heat source, for each optic-isolated chamber, are also provided within the housing. A cell, having a plurality of gas inputs and gas outlets, for holding a sample to be tested, is provided within the housing for each chamber. The gas inputs and outputs are distributed about the cell so as to disperse gas evenly about the material to be tested. The apparatus is used to count the number of photons which escape from a test sample as various oxidation conditions are employed.

26 Claims, 7 Drawing Sheets

APPARATUS AND METHOD FOR ACCELERATED TESTING OF MATERIALS

FIELD OF THE INVENTION

The present invention concerns a novel apparatus for accelerated testing of materials by thermal oxidation. Specifically, by measuring the amount of light emitted by a sample material in the process of thermal oxidation various characteristics of the material may be determined.

BACKGROUND OF THE INVENTION

Most materials exposed to daily conditions of oxidation, including heat and exposure to air, are likely to oxidize and lose strength. Further, exposure causes the appearances of materials to be marred. Manufacturers of materials endeavor to produce products that hold color and physical integrity. For example, some manufacturers include various oxidation resistant additives to their polymer material to increase their durability. However, the amount of the additive and the associated increase in durability are often hard to gauge.

Chemiluminescence analysis is a process whereby the amount of light emitted from any material subjected to oxidizing agents is considered as a measure of the strength and durability of the material. The discovery of the relationship between the generation of photons or light emissions and strength and durability of materials has prompted material specialists, polymer producers, manufacturers, suppliers and others to try and find a manner of counting these photons and correlating that data with the deterioration of the material.

An apparatus for the determining the oxidative stability of polymers, including the use of the process of chemiluminescence is described in Broutman et al., U.S. Pat. No. 4,350,495. Further, Japanese Kokai document No. 193943/1996 discloses a similar device with a means for testing materials while creating linear deformations in the polymer sample.

Broutman et al. state, in the background of the invention section of the '495 patent, that the use of chemiluminescence to determine these characteristics of polymers was first published about 20 years before the application for the '495 patent. The '495 patent proceeds to explain that for those twenty years no commercial installation of this type had been offered and attempted to offer the device of the '495 patent as such an installation. The device of the '495 patent is described as a device for the counting of photons in a chemiluminescence application. We have found that a device manufactured from the '495 patent has certain deficiencies which may result in non-reproducible and unreliable results.

The apparatus described in the '495 patent has a single heated plate for heating all polymer samples located inside of the testing apparatus. This design eliminates the possibility of conducting tests of individual polymer samples at different temperatures simultaneously, because the temperature of the sample and gas utilized for oxidation process depends on the temperature of a single heating element. Because of the large size of the heating element, or plate, described in the '495 patent, cells are located in zones with non-uniform temperature. The device of the '495 patent does not provide uniform heat transfer and diffusion process of oxygen to the surface of the testing polymer.

Another disadvantage of the '495 design is that it requires that the photomultiplier be rotated relatively to the samples, set in a fixed location in the device, for measuring light intensity. The design described in the '495 patent, although shown as being able to test multiple samples simultaneously, makes it impossible to simultaneously register data from a number of individual samples. As a result, some of the experimental data is lost because of the high speed of oxidation and physical-chemical transformation of the material. Often this speed of transformation is less than the time necessary for the rotation of the samples so that measurements can be taken plus the time needed to stabilize the photomultiplier so that it can accurately record data.

It is therefore an object of the present invention to provide a device and method for accurately measuring the light emitted from a test material during oxidation. It is a further object of the present invention to provide a device and method that allow for reliable and reproducible chemiluminescence testing.

Other objects and advantages of the present invention will become apparent as the description proceeds.

SUMMARY OF THE INVENTION

In accordance with the present invention, an apparatus for the testing of materials by thermal oxidation is provided. The apparatus comprises a housing having an optic-isolated chamber, a photon counting photomultiplier and a heat source are located within the housing. A cell, having a plurality of gas inputs and gas outlets, for holding a sample to be tested, is provided within the housing. The gas inputs and outputs are distributed about the cell so as to disperse gas about the material to be tested.

In the illustrative embodiment, the cell is provided with four gas inputs and four gas outlets, each spaced equidistant from each other in such a manner as to allow an even distribution of oxidizing gas. Gas enters the cell from below rises above the test sample, and is then pushed down onto the sample. The gas is then evacuated out of four evenly distributed exhaust holes in the cell.

In the illustrative embodiment, four cells are provided in a housing, each able to conduct separate, independent tests. Each cell, in the machine of the illustrative embodiment, is provided with its own photomultiplier, its own gas inputs and gas outputs, and its own heat source. In the illustrative embodiment, the cell, photomultiplier and heat source are coaxially aligned. As a result of providing each cell with independent means of testing materials, each cell produces more reproducible results.

The cells of the illustrative embodiment are provided with a convex shaped lens between the test sample and the photomultiplier. The use of this lens allows for the focusing of the photons on to the photomultiplier to allow for a more accurate reading of escaping photons. Further, the device of the illustrative embodiment is provided with a high speed shutter, similar to those found on cameras and an infrared filter. Both the shutter and the filter are designed to protect the photomultiplier from exposure to harmful light and heat which is extraneous to the desired data but which are present during various times in the testing, pretesting and post testing procedures.

Each cell in the illustrative embodiment is provided with its own, independently regulated, heating element. The heating element is coaxial with the gas input lines and the cell, providing for uniform heating of the cell and heating of the gas prior to its entry into the cell, so that the desired temperature is accurately maintained.

Further, in accordance with the present invention a method for testing of materials by thermal oxidation is described, including the steps of providing the device as described herein and placing a sample of material to be tested within the cell of the device, placing the cell in the optic-isolated chamber and distributing an oxidizing gas through the gas inputs such that the sample material is consistently contacted by the oxidizing gas, and counting the photons released from said sample with the photomultiplier.

A more detailed explanation of the invention is provided in the following description and claims and is illustrated in the accompanying drawings.

DETAILED DESCRIPTION OF THE ILLUSTRATIVE EMBODIMENT

Figure 1:
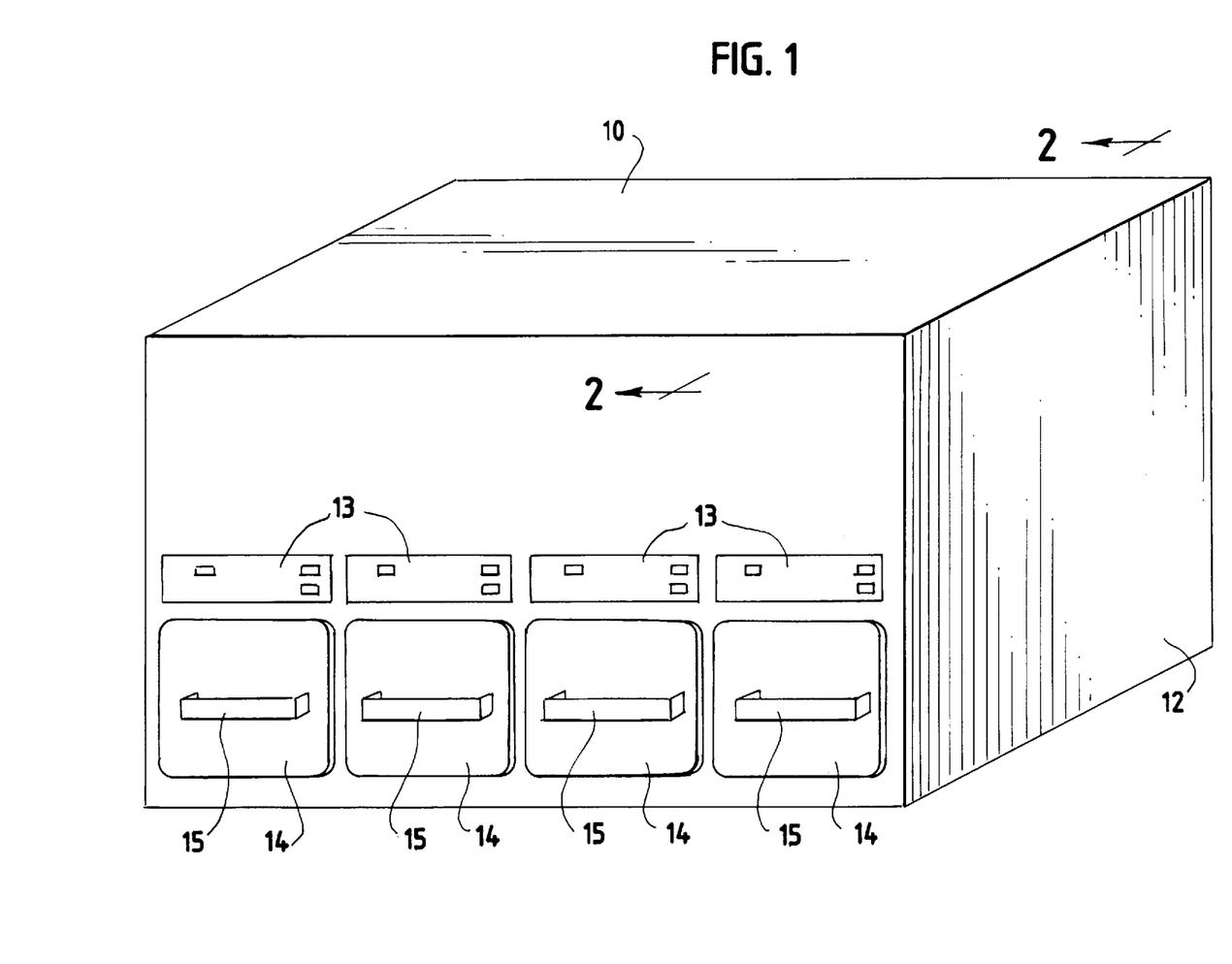
FIG. 1 is a perspective view of the device of the present invention.
Figure 2:
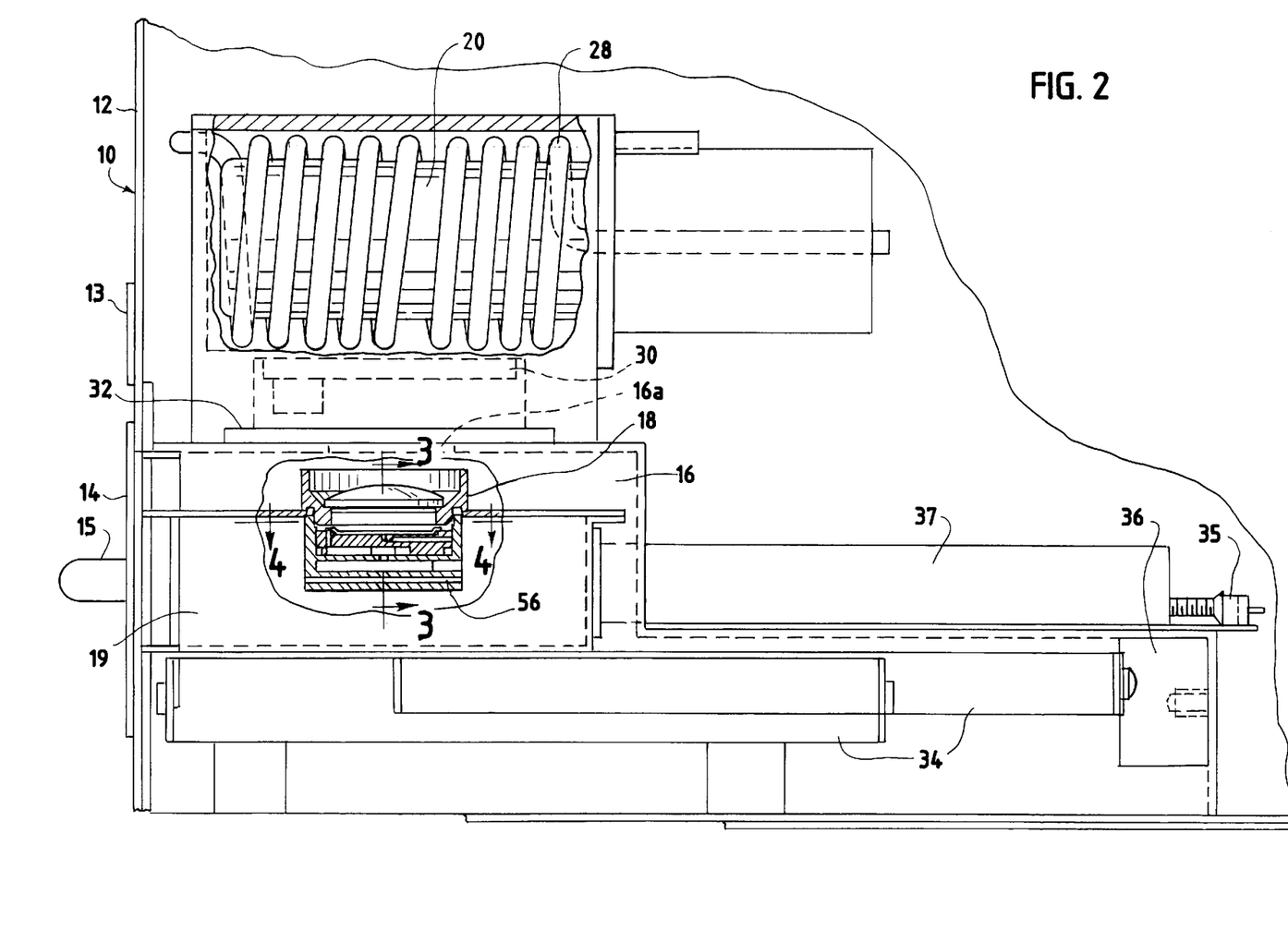
FIG. 2 is a cross sectional view, taken along the plane of the line 2—2 of FIG. 1, of the optic-chamber area of the device of the present invention.

Referring to the drawings, FIG. 1 is a perspective view of an apparatus 10 for testing materials by thermal oxidation of the present invention. The apparatus 10 comprises a housing 12 containing, in the illustrative embodiment, four drawers 14; each drawer 14 having a handle 15 and containing an optic-isolated chamber 16 (FIG. 2). Each drawer is provided with a display panel 13 (FIG. 1) providing such information as status of the drawer and the type of gas presently in use in the drawer. While four drawers are shown in the illustrative embodiment, it is to be understood that a different number of drawers can be used without departing from the novel scope of the present invention.

One of the optic isolated chambers 16 and a portion of the interior of housing 12 is shown in detail in FIG. 2. In FIG. 2 the device of the present invention is shown in a test position. It can be seen, that within housing 12, a cell 18 and a photon-counting photomultiplier 20 are provided. When drawer 14 is in its test position, as shown in FIG. 2, photomultiplier 20 and cell 18 are aligned. Cell 18 is installed in the center of thermoinsulation elements 19 on drawer 14. The top surface of optic-isolation chamber 16 defines an opening 16a allowing light transmission between photomultiplier 20, optic-isolation chamber 16 and cell 18.

Photomultiplier 20 is provided with a cooling coil 28, whose use will be described below. A shutter 30 and an infrared heat absorbing filter 32 are provided between photomultiplier 20 and cell 16. Shutter 30 provides the ability to optically isolate photomultiplier 20 to prevent damage, from light and heat, when drawer 14 is opened. Infrared heat absorbing filter 32 prevents damage to photomultiplier 20 from any infrared wave length radiation. Slides 34 are provided to allow the user to open drawer 14 so as to access cell 18. A door switch 35 and a magnetic lock mechanism 36, to secure drawer 14 in its closed position during testing, are also provided. FIG. 2 further shows a tube 37, to house gas tubing, heater leads and thermocouple leads (all not shown). A heater 56 is provided in cell 18 and its use will be explained below.

Figure 3:
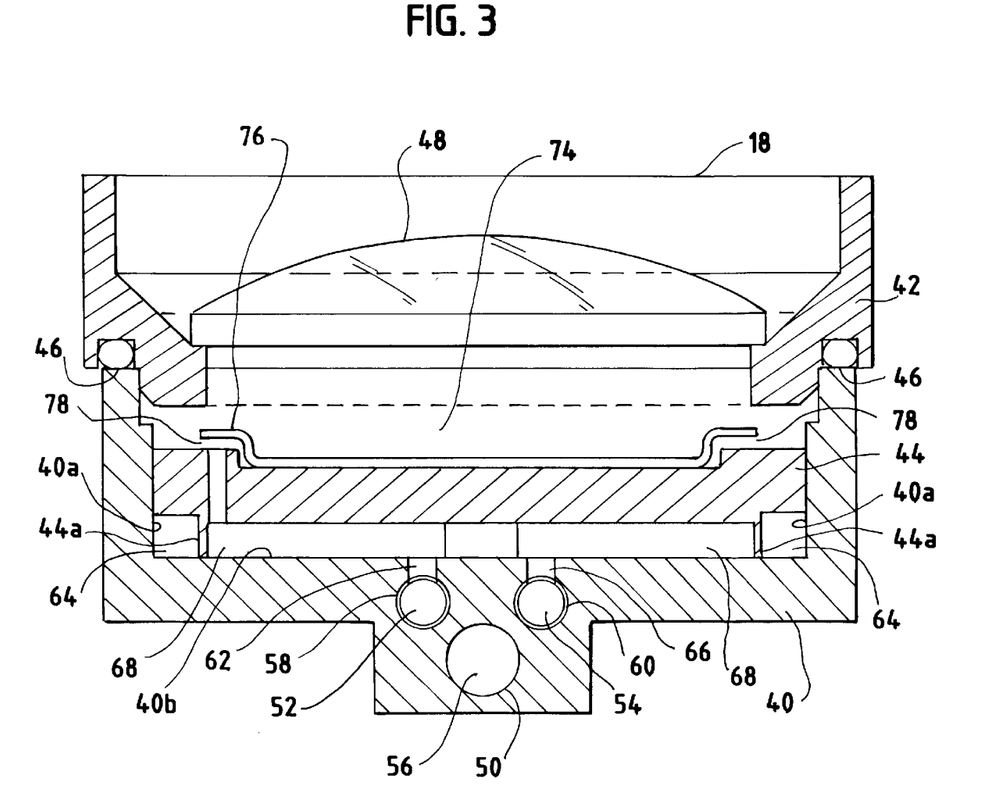
FIG. 3 is an enlarged cross sectional view, taken along the plane of the line 3—3 of FIG. 2, of a testing cell of the present invention.

Cell 18 can be seen in greater detail in FIG. 3. FIG. 3 is a cross-section of cell 18, taken along the plane of line 3—3 in FIG. 2. Cell 18 comprises a base 40, cap 42 and an insert 44 installed in base 40 in such a manner that the bottom part 44a of insert 44 is in contact with base 40. Base 40 and cap 42 are screwed together in a conventional manner and are sealed, in a gas-tight manner, by sealing element 46. As shown in FIG. 3, sealing element 46 is an O-ring type seal, made of rubber-type material, however, a C-type seal, made of metallic materials has also been used successfully, and other types of sealing rings can be used without departing from the novel scope of the present invention. A lens 48 is installed into cap 42.

Figure 5:
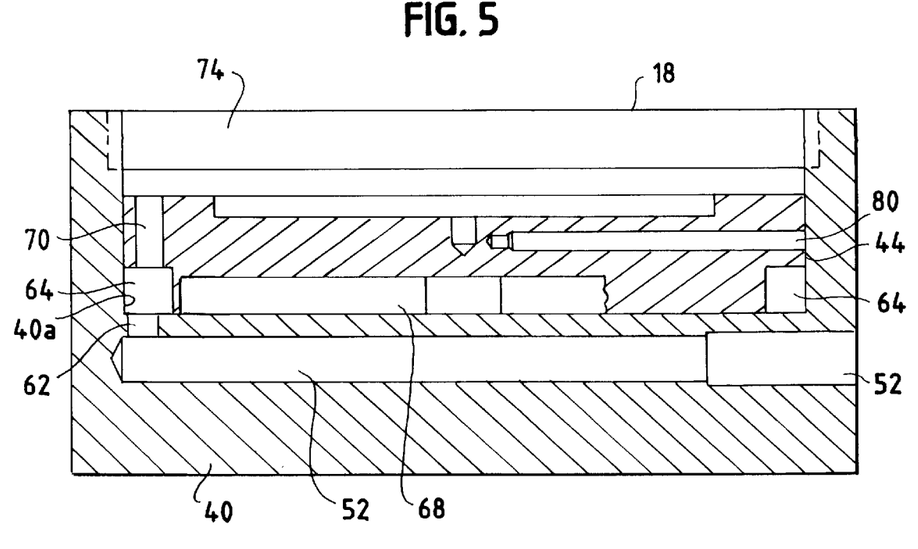
FIG. 5 is an enlarged cross sectional view of a portion of a testing cell, taken along plane 5—5 of FIG. 4.
Figure 6:
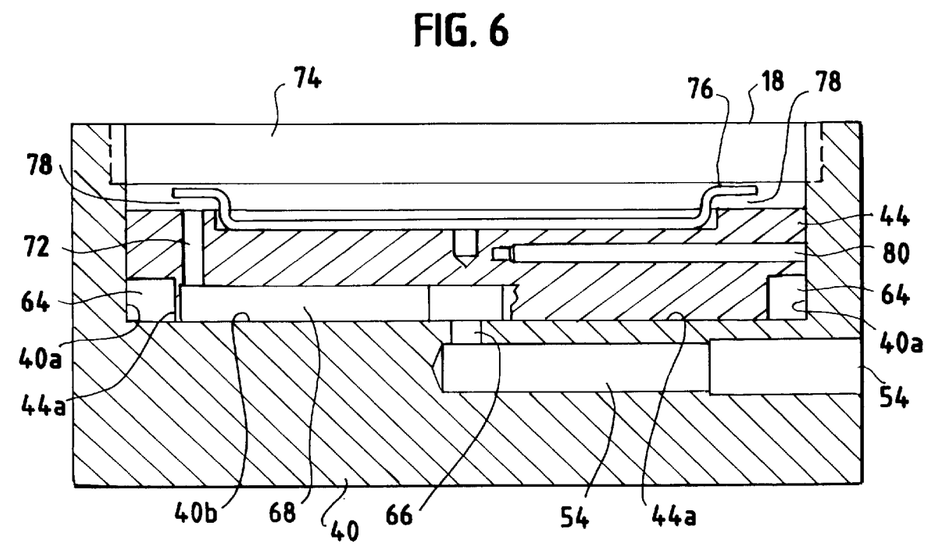
FIG. 6 is an enlarged cross sectional view of a testing cell, taken along the plane of line 6—6 of FIG. 4.

As shown in FIG. 3, base 40 defines three parallel horizontal channels, 50, 52 and 54. Channel 50 is used for the installation of a heater 56. Because channels 50 and 52 are placed in close proximity and run parallel within base 40, gas entering cell 18 is warmed by heater 56 to the test temperature, thereby assisting in the even distribution of heat to the test specimen. Channel 52 is used for connection of a gas supply line 58 and channel 54 is used for connection of an exhaust gas line 60. A vertical channel 62 connects channel 52 with a closed pocket 64, providing passage for incoming gases into cell 18. A more detailed drawing of the connection of incoming gas to the cell 18 is shown in FIG. 5, and will be explained in greater detail below. Vertical channel 66 connects horizontal channel 54 with internal cavity 68, providing the necessary path for the removal of exhaust gases from internal cavity 68. A more detailed drawing of the connection of internal cavity 68 and channel 54 is shown in FIG. 6, and will be explained in greater detail below. Closed pocket 64 and internal cavity 68 are created by the specific design of insert 44.

Figure 4:
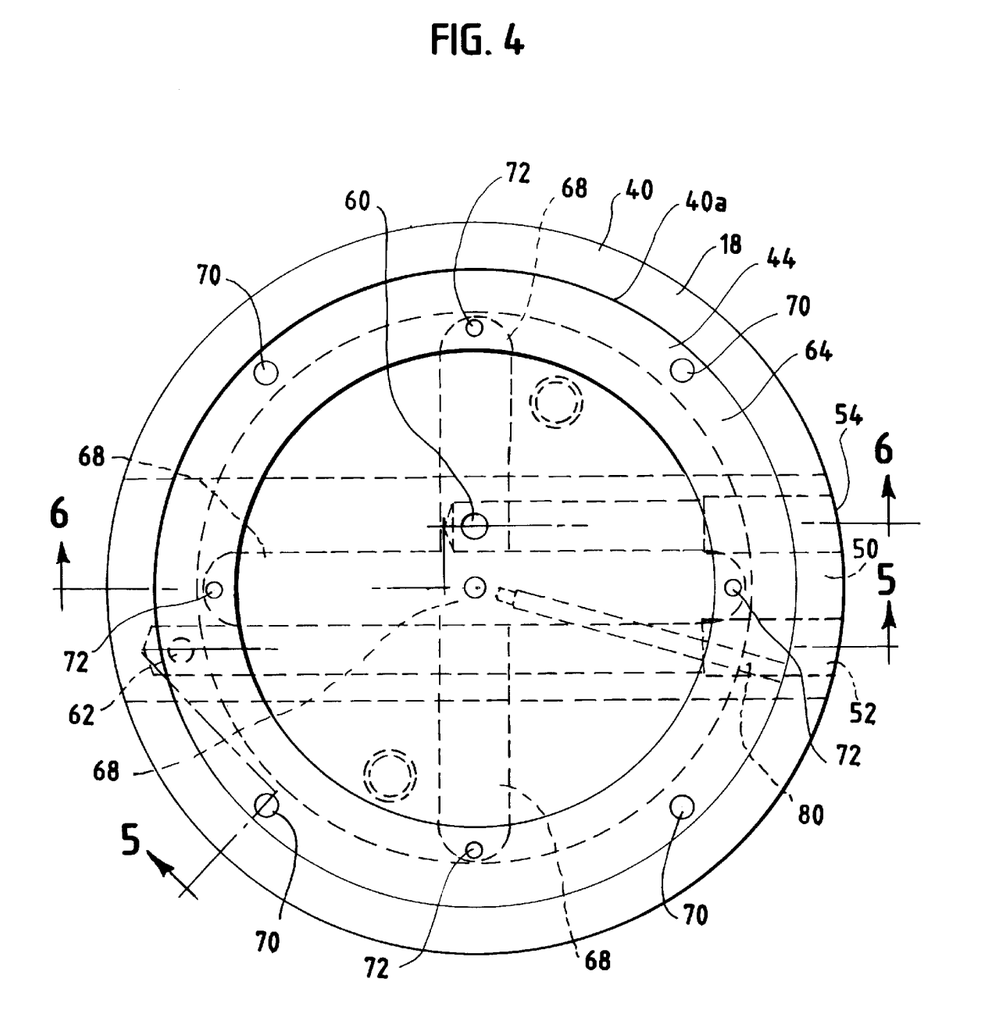
FIG. 4 is an enlarged cross sectional view of a testing cell, taken along the plane of line 4—4 of FIG. 2.

FIG. 4 is a cross section of cell 18, taken along the plane of line 4—4 in FIG. 2, and more clearly shows the details of base 40 and insert 44. As can be seen in FIG. 4, closed pocket 64 forms a ring about the circumference of insert 44, with wall 40a of base 40 forming the exterior wall of the closed pocket 64 ring. Internal cavity 68 is a cross-shaped cavity, formed within insert 44 and having wall 40b (FIG. 3) as its base. The installation of insert 44 into base 40 causes closed pocket 64 and internal cavity 68 to be closed and separated from each other. The installation of insert 44 provides separate paths for incoming and exhaust gases, respectively. FIG. 4 further shows gas inputs 70 and gas outlets 72, which will be explained in greater detail below.

FIG. 5 is a cross-sectional view of cell 18 taken along the plane of line 5—5 of FIG. 4. FIG. 6 is a cross-sectional view of a cell 18 taken along the plane of line 6—6 of FIG. 4. In FIG. 5 it can be seen that gas pushed into cell 18 at channel 52, proceeds to vertical channel 62 and into the closed pocket 64 ring. Gas in the closed pocket 64 ring proceeds to gas inputs 70 where it is distributed in testing compartment 74. The upward pressure of gas through inputs 70, causes the gas, warmed to testing temperature as described above, to push upwardly into compartment 74 where it is dispersed downwardly, at pressure, onto a testing sample, not shown, resting on a cuvette 76 (shown in FIG. 3). The gas is then, under the pressure of more incoming gas, caused to flow away from the test sample towards the gap 78 between cuvette 76 and the top surface of insert 44 (shown in FIG.

6). As shown in FIG. 6, the exhaust gas is caused to flow down gas outlet 72, into internal cavity 68, down vertical channel 66, out of channel 54 and out of cell 18.

As can be seen, in FIG. 4, four gas inputs 70 and four gas outlets 72 are used in the illustrative embodiment of the present invention and are located with equal angular displacement relative to each other. This design provides uniform gas distribution inside of cell 18.

Cuvette 76, as shown in FIG. 6, is a dish-like element, having a raised rim, used to hold a test sample within cell 18. Cuvette 76 can be made of aluminum or stainless steel, or other non-reactive materials. Thermocouple 80 is installed in the base 40 and provides a measurement of the temperature of the base 40 for the temperature control system. Thermocouple 80 further provides a means to calibrate heater 56, in a manner known in the art.

Figure 7:
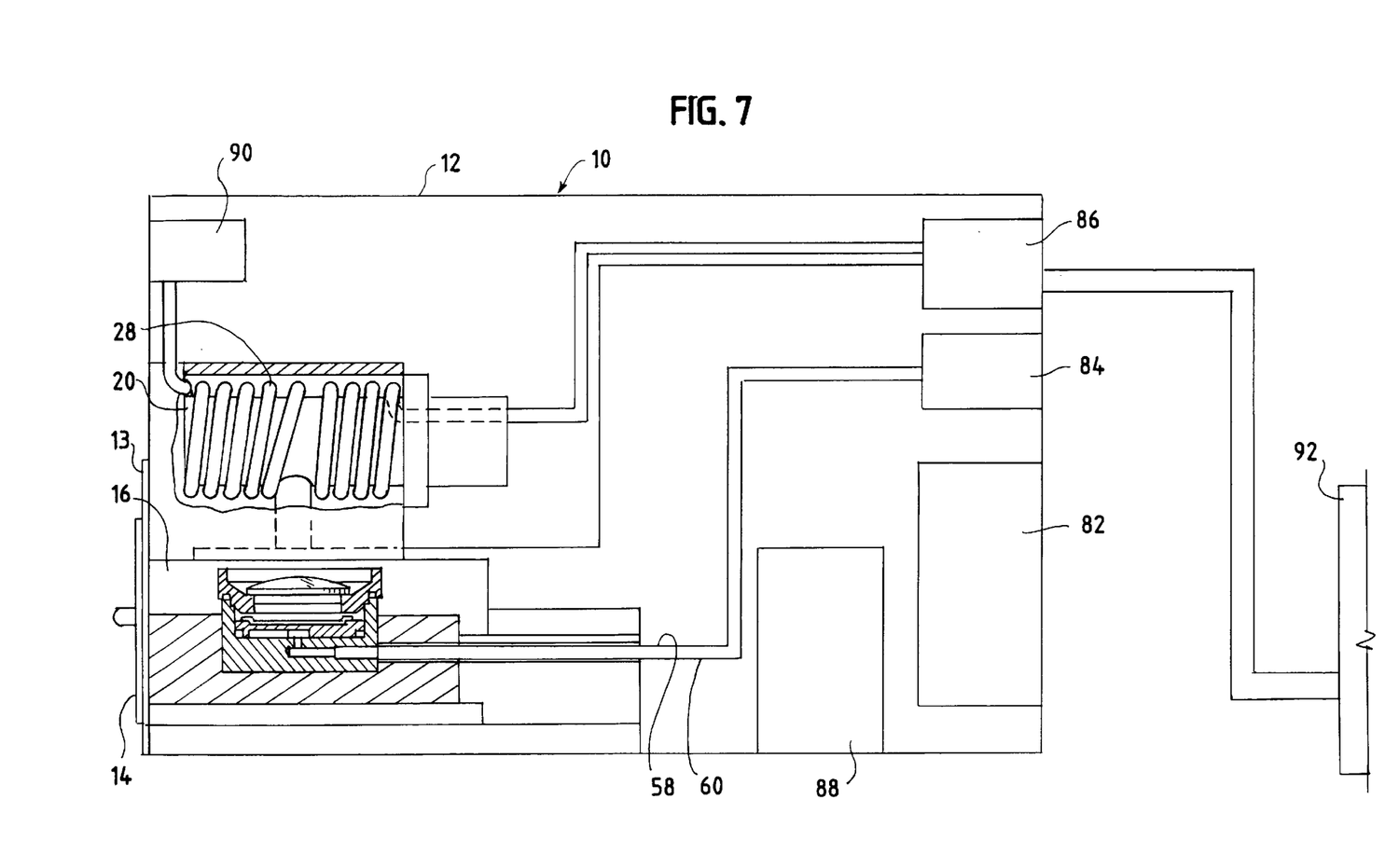
FIG. 7 is a cross sectional view, taken along the plane of line 2—2 of FIG. 1.

FIG. 7 is a cross-sectional view of the housing of the present invention, taken along the plane of line 2—2 of FIG. 1. In FIG. 7 it can be seen that housing 12 further comprises a controller 82, a gas valve control module 84, a power supply block 86, a gas flow sensor 88, a water control system 90 and a computer 92. Controller 82 provides control of the temperature and gas flow for each individual cell 18, amplifies the signal of each photomultiplier 20, and communicates with computer 92.

The device of the present invention can be used to test samples of a variety of materials, including but not limited to: ABS, ABS/polycarbonate blends, antioxidants, edible oils, elastomers, epoxy resins, jet fuels, lubricants, metal deactivators, nylon 66, pharmaceuticals, poly (ethylene oxide), poly (ethylene terephthalate), poly (methyl methacrylate), poly (vinyl chloride), polyacetals, polybutadiene, polycarbonate, polycylopentadiene, polyester-ther copolymers, polyethylene, polyisobutylene, polypropylene, polystyrene. Further, analysis of food contamination, purity of chemical solutions and biomedical research (such as CL emissions from blood cells) can also be examined using the device of the present invention.

Figure 8:
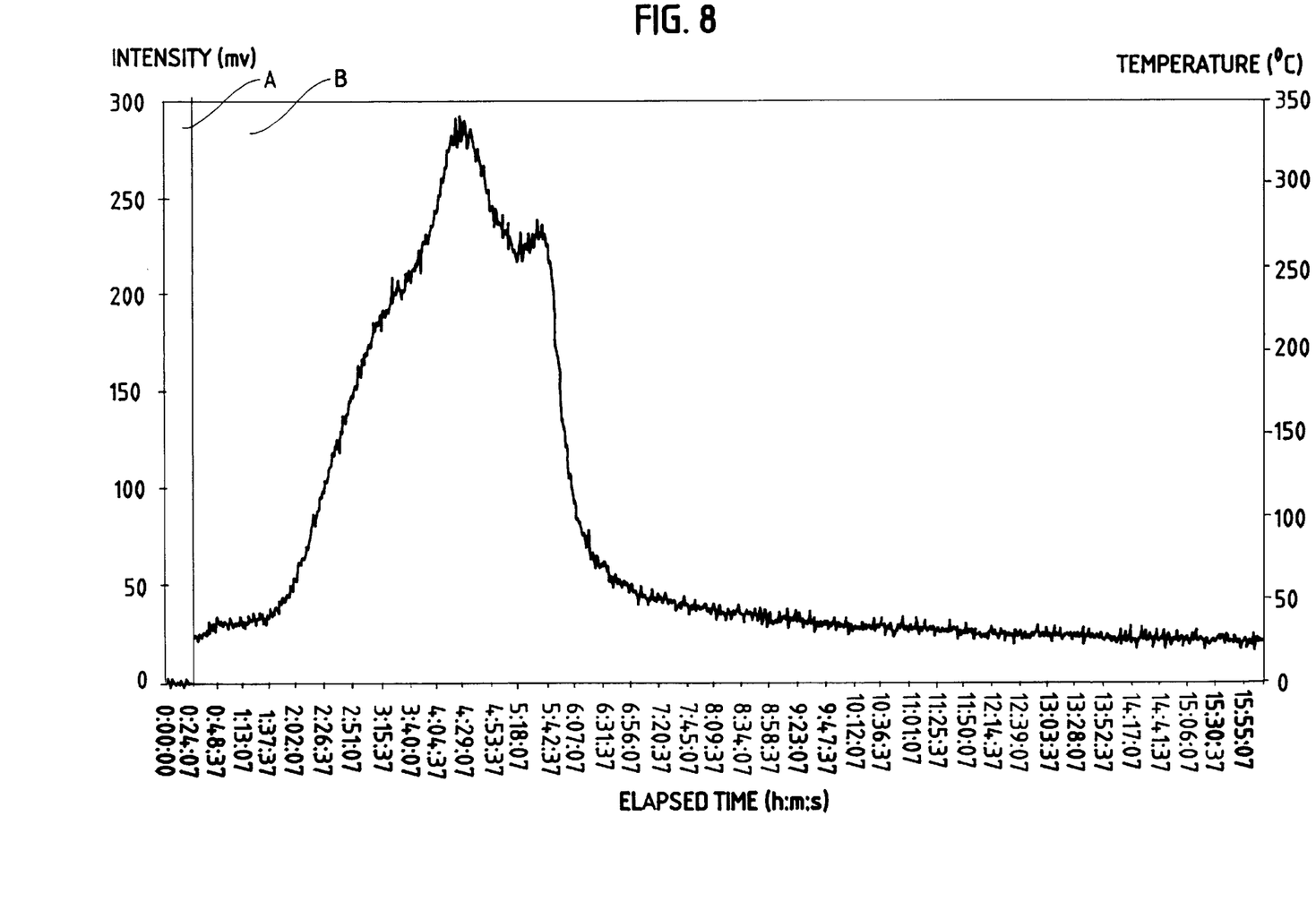
FIG. 8 is a plot of test results as provided by the device of the present invention.

In the operation of the present invention, referring to FIG. 3 and FIG. 4 a sample material is placed on the surface of the cuvette 76 (FIG. 3), installed on the top of the insert 44 inside of the cell 18. Lens 48 and cap 42 are connected to the base 40, compressing sealing element 46, creating a hermetically closed space 74 (see FIG. 3). Before starting the test, test temperature, test gas types, gas flow rate and heating ramp data are entered into computer 92. Computer 92, through its connection with controller 82, starts the test, turns on the heater 56 and ramps the temperature up to the selected test temperature (see FIG. 8). At the same time the gas valve control module 84 provides flow of nitrogen, or other inert gas, into cell 18. The incoming nitrogen is heated up to the selected test temperature, as it runs parallel to heater 56 in gas channel 52. Simultaneously, the heat is transferred from the heater 56 through the base of cell 18 and cuvette 76 to the sample located on the top of cuvette 76. After reaching the test temperature and stabilization at this temperature for 45–60 minutes, the gas valve control module 84 stops the flow of nitrogen and starts the flow of oxygen, or other oxidizing agent, starting the process of oxidation. Cooling coils 28, fed with chilled water from water control system 90, keep photomultiplier 20 cool while cell 18 and the gas being put into the cell 18 are heated by heater 56. Photomultiplier 20 registers the light emitted by the sample and generates an analog signal proportional to the intensity of light. Controller 82 transforms the analog signal of photomultiplier 20 into digital form, and transmits the data to the computer 92. Computer 92 provides graphic representations of test results, as shown in FIG. 8. FIG. 8 shows the results of a test on a polyvinyl chloride-flexible material. The test, done at a constant temperature of 160° C., using oxygen as the oxidating gas, shows peak intensity of photons at between 4 hours 4 minutes and 4 hours 53 minutes after testing began. Zone A of the graph, FIG. 8, shows the results during the temperature ramping phase (constant increase of temperature from room temperature up to testing temperature) using nitrogen gas within cell 18. Zone B of the graph, FIG. 8, shows results after the testing temperature had been achieved and oxygen flow had begun.

Computer 92 provides control of the apparatus and makes all necessary calculations on defining the parameters of oxidation. As a specific example, although no limitation is intended, the parameters of oxidation can be calculated by the following procedure:

a) defining the maximum acceptable degree of oxidation for the tested polymer-β from analysis of the function of specific properties of the polymer material (strength, color, etc.) from the degree of oxidation: Parameter β characterizes the maximum acceptable amount of oxidized fractional material;

b) performing the process of oxidation of material in the above described device while measuring the intensity of light emitted by the polymer and time of oxidation;

c) calculating the integral:

$$I_{max} = \int_0^{t_{max}} i(t)dt$$

reflecting the amount of oxidized fraction of material up to the moment of maximum intensity of oxidation. Where i(t) is a function of the light emitted by the polymer from the time of oxidation (t), received from experimental results (experimental curve, See FIG. 8); and $t_{max}$ is the time from the beginning of oxidation until the moment of achieving maximum intensity of the emitted light;

d) calculating the value of $I_t = \beta I_{max}$ (reflects the maximum acceptable amount of oxidized fraction of the polymer material from the point of view of the physical-mechanical properties of the polymer) and finding from the results of the measurements the value of the critical time of oxidation "$t_{critical}$" at which:

$$i = \int_0^{t_{critical}} i(t)dt = I_t$$

The received data on critical time of oxidation can be used for design of the polymer material with the requested physical-mechanical properties.

The use of the above described apparatus and method of testing, in association with an understanding of the physical properties of the test sample, will provide the manufacturer of materials the ability to reliably design materials for various oxidation conditions.

Although an illustrative embodiment of the invention has been shown and described, it is to be understood that various modifications and substitutions may be made by those skilled in the art without departing from the novel spirit and scope of the invention.

What is claimed is:

1. An apparatus for testing of materials by thermal oxidation comprising:

a housing;

an optic-isolated chamber;

a photon counting photomultiplier within said housing;

a heat source; and, a cell, having a plurality of gas inputs and gas outlets within said cell, for holding a sample of material to be tested;

said gas inputs and gas outlets being distributed within said cell so as to direct the dispersement of gas about a test material.

2. The apparatus for testing materials of claim 1, wherein the photomultiplier, heat source and cell are coaxially aligned.

3. The apparatus for testing materials of claim 1, wherein said gas inputs and gas outlets are evenly distributed about said cell.

4. The apparatus for testing materials of claim 1, wherein a controller, for controlling heat, said photomultiplier and gas input is provided in said housing.

5. The apparatus for testing materials of claim 1, wherein said cell includes a convex lens at an upper location of said cell.

6. The apparatus for testing materials of claim 1, wherein said photomultiplier is protected by an infrared heat absorbing filter.

7. The apparatus for testing materials of claim 1, wherein said gas is distributed down onto said test material.

8. The apparatus for testing materials of claim 1, wherein said gas is distributed evenly about said test material.

9. The apparatus for testing materials of claim 1, including gas feed lines located proximate said heat source such that gas fed to said gas inputs is warmed substantially to test temperature prior to contacting said test material.

10. An apparatus for testing of materials by thermal oxidation comprising:

a housing;

an optic-isolated chamber;

a photon counting photomultiplier within said housing;

a heat source; and, a cell, having a plurality of gas inputs and gas outlets within said cell, for holding a sample of material to be tested;

said photomultiplier, heat source and cell being coaxially aligned within said housing;

said gas inputs and gas outlets being evenly distributed within said cell so as to direct the dispersement of gas about a test material.

11. The apparatus for testing materials of claim 10, including gas feed lines located proximate said heat source such that gas fed to said gas inputs is warmed substantially to test temperature prior to contacting said test material.

12. The apparatus for testing materials of claim 10, wherein a controller, for controlling heat, said photomultiplier and gas input is provided in said housing.

13. An apparatus for testing of materials by thermal oxidation comprising:

a housing;

an optic-isolated chamber;

a photon counting photomultiplier within said housing;

a computer;

a heat source;

a controller for controlling said heat source, photomultiplier and gas inputs, said controller being responsive to inputs from said computer; and, a cell, having a plurality of gas inputs and gas outlets within said cell, for holding a sample of material to be tested and a convex lens;

said photomultiplier, heat source and cell being coaxially aligned within said housing;

said gas inputs and gas outlets being evenly distributed within said cell so as to direct the dispersement of gas about a test material.

14. The apparatus for testing materials of claim 13, wherein said gas is distributed evenly about said test material.

15. The apparatus for testing materials of claim 13, including gas feed lines located proximate said heat source such that gas fed to said gas inputs is warmed substantially to test temperature prior to contacting said test material.

16. The apparatus for testing materials of claim 13, wherein said photomultiplier is protected by an infrared heat absorbing filter.

17. An apparatus for testing materials by thermal oxidation comprising:

a housing;

a plurality of optic-isolated chambers within said housing, each of said optic-isolated chambers including a heat source and a cell for holding a sample to be tested;

a photon counting photomultiplier associated with each of said optic-isolated chambers;

said apparatus being operable to conduct tests in any number of said plurality of optic-isolated chambers independently of the others.

18. The apparatus for testing materials of claim 17, wherein each of said cells for holding samples to be tested comprises a plurality of gas inputs and gas outlets, distributed about said cell, so as to disperse gas about a test material.

19. The apparatus for testing materials of claim 18, wherein said gas inputs and gas outlets are evenly distributed about said cell.

20. The apparatus for testing materials of claim 18, including gas feed lines located proximate each of said heat sources such that gas fed to said gas inputs is warmed substantially to test temperature prior to contacting said test material.

21. The apparatus for testing materials of claim 17, wherein each photomultiplier is coaxially aligned with a heat source and a cell.

22. The apparatus for testing materials of claim 17, wherein each cell includes a convex lens at an upper location of said cell.

23. The apparatus for testing materials of claim 17, wherein each of said photomultipliers is protected by an infrared heat absorbing filter.

24. An apparatus for testing materials by thermal oxidation comprising:

a housing;

a plurality of optic-isolated chambers within said housing, each of said optic-isolated chambers including a heat source and a cell for holding a sample to be tested;

a photon counting photomultiplier associated with each of said optic-isolated chambers, coaxially aligned with said heat source and said cell;

each cell having a convex lens at an upper location of said cell and comprising a plurality of gas inputs and gas outlets evenly distributed within said cell, so as to direct the dispersement of gas about a test material;

said apparatus being operable to conduct tests in any number of said plurality of optic-isolated chambers independently of the others.

25. A method for testing of materials by thermal oxidation including the steps of:

provi­ding a housing;

providing an optic-isolated chamber;

providing a photon counting photomultiplier within said housing;

providing a heat source;

providing a cell, having a plurality of gas inputs and gas outlets within said cell, for holding a sample of material to be tested;

placing a sample of material to be tested within said cell;

placing said cell in said optic-isolated chamber;

distributing an oxidizing gas through said plurality of gas inputs such that said sample material is consistently contacted by the oxidizing gas; and counting photons released from said sample with said photomultiplier.

26. A method for testing of materials by thermal oxidation including the steps of:

providing a housing;

providing an optic-isolated chamber;

providing a photon counting photomultiplier within said housing;

providing a heat source;

providing a cell, having a plurality of gas inputs and gas outlets within said cell, for holding a sample of material to be tested;

placing a sample of material to be tested within said cell;

placing said cell in said optic-isolated chamber;

distributing an oxidizing gas through said plurality of gas inputs such that said sample material is evenly contacted by the oxidizing gas; and counting photons released from said sample with said photomultiplier.

* * * * *